(12) United States Patent
Ellies et al.

(10) Patent No.: US 8,513,274 B2
(45) Date of Patent: Aug. 20, 2013

(54) ELLIPTICINE COMPOUNDS FOR TREATING OBESITY

(75) Inventors: Debra Ellies, Parksville, MO (US); William Rosenberg, Overland Park, KS (US)

(73) Assignee: Etzem, Inc., Kansas City, KS (US)

(*) Notice: Subject to any disclaimer, the term of this patent is extended or adjusted under 35 U.S.C. 154(b) by 280 days.

(21) Appl. No.: 12/723,884

(22) Filed: Mar. 15, 2010

(65) Prior Publication Data
US 2010/0249171 A1    Sep. 30, 2010

Related U.S. Application Data

(60) Provisional application No. 61/160,805, filed on Mar. 17, 2009.

(51) Int. Cl.
*A61K 31/44*    (2006.01)
*A61K 31/40*    (2006.01)

(52) U.S. Cl.
USPC ............ 514/279; 514/284; 514/343; 514/410

(58) Field of Classification Search
USPC .................... 514/279, 284, 343, 410
See application file for complete search history.

(56) References Cited

U.S. PATENT DOCUMENTS

2007/0027175 A1    2/2007    Shaugnessy et al.

OTHER PUBLICATIONS

Stiborova M. et al. "Molecular Mechanisms of Antineoplastic Action of an Anticancer Drug Ellipticine". Biomed Pap Med Fac Univ Palacy Olomouc Czech Repub. 2006, 150(1):13-23.*

Stiborová et al.; "Role of hepatic cytochromes P450 in bioactivation of the anticancer drug ellipticine: studies with the hepatic NADPH:cytochrome P450 reductase null mouse"; *Toxicol. Appl. Pharmacol.*; 226(3):318-327 (Feb. 2008) Epub Sep. 26, 2007.

Stiborová et al.; "Formation and persistence of DNA adducts of anticancer drug ellipticine in rats"; *Toxicology*; 236(1-2):50-60 (Jul. 2007) Epub Apr. 7, 2007.

Stiborová et al.; "The anticancer drug ellipticine forms covalent DNA adducts, mediated by human cytochromes P450, through metabolism to 13-hydroxyellipticine and ellipticine N2-oxide"; *Cancer Res.*; 64(22):8374-8380 (2004).

The International Search Report from PCT/US2010/027337.

* cited by examiner

*Primary Examiner* — Renee Claytor
(74) *Attorney, Agent, or Firm* — Kilpatrick, Townsend & Stockton LLP

(57) ABSTRACT

The present invention provides a method of reducing body weight in a subject in need thereof, by administering to the subject a therapeutically effective amount of a compound of Formula I:

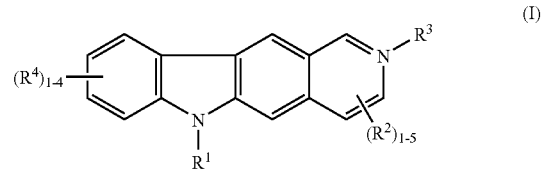

(I)

In Formula I, $R^1$ is H, $C_{1-6}$ alkyl, or $C_{1-6}$ alkyl-aryl. Each of $R^2$ and $R^4$ of Formula I are independently H, halogen, $C_{1-6}$ alkyl, $C_{1-6}$ haloalkyl, $C_{2-6}$ alkenyl, $C_{2-6}$ alkynyl, $C_{1-6}$ haloalkoxy, —$OR^{2a}$, —$SR^{2a}$, —$C(O)R^{2a}$, —$C(O)OR^{2a}$, —$C(O)NR^{2a}R^{2b}$, —$NR^{2a}R^{2b}$, $C_{1-6}$ alkyl-$NR^{2a}R^{2b}$, —$N(R^{2a})C(O)R^{2b}$, —$N(R^{2a})C(O)OR^{2b}$, —$N(R^{2a})C(O)NR^{2a}R^{2b}$, —$OP(O)(OR^{2a})_2$, —$S(O)_2OR^{2a}$, —$S(O)_2NR^{2a}R^{2b}$, —CN, —$NO_2$, cycloalkyl, heterocycloalkyl, aryl or heteroaryl. Each of $R^{2a}$ and $R^{2b}$ of Formula I are independently H, $C_{1-6}$ alkyl, $C_{1-10}$ heteroalkyl or $C_{1-6}$ alkyl-aryl. $R^3$ of Formula I is absent, $C_{1-6}$ alkyl or N-oxide. The compounds include the salts, hydrates and isomers thereof. The present invention also provides methods for the treatment of obesity and disorders related to obesity and higher than recommended percentage body fat, such as type II diabetes.

16 Claims, 1 Drawing Sheet

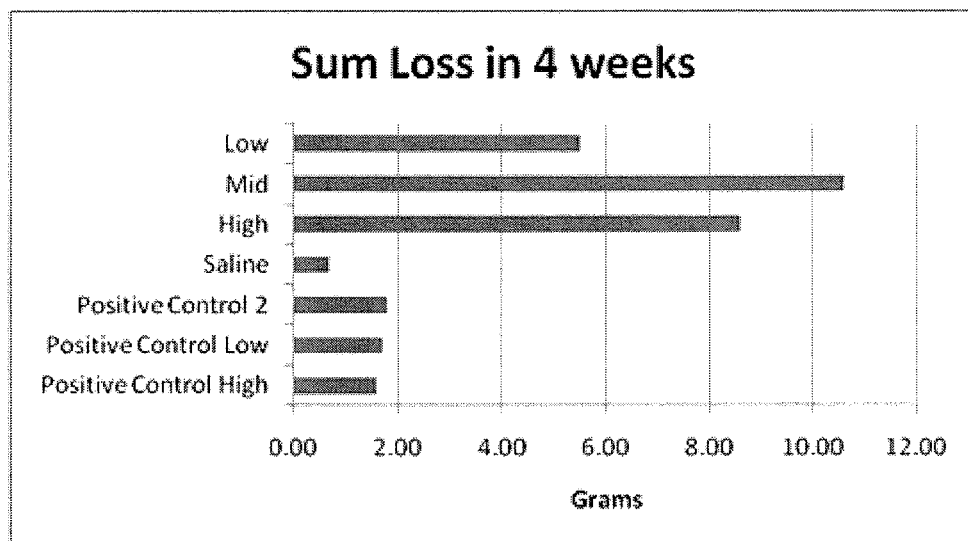

ELLIPTICINE COMPOUNDS FOR TREATING OBESITY

CROSS-REFERENCES TO RELATED APPLICATIONS

This application claims priority to U.S. Provisional Application No. 61/160,805, Mar. 17, 2009, which is incorporated in its entirety herein for all purposes.

BACKGROUND OF THE INVENTION

The prevalence of obesity has risen significantly in recent decades in developed countries (Fiegal et al. (1998) *Int. J. Obesity* 22:39-47; Mokdad et al. (1999) *JAMA* 282:1519-1522). Because obesity is associated with a significantly elevated risk for type 2 diabetes, coronary heart disease, hypertension, and numerous other major illnesses, and overall mortality from all causes (Must et al. (1999) *JAMA* 282: 1523-1529; Calle et al. (1999) *N. Engl. J. Med.* 341:1097-1105), weight reduction is critical for the obese patient (Blackburn (1999) *Am. J. Clin. Nujtr.* 69:347-349, Galuska et al. (1999) *JAMA* 282:1576). Evidence suggests that pharmacotherapy can enhance weight loss when combined with interventions aimed at changing life style (National Heart, Lung and Blood Institute, Clinical guidelines on the identification, evaluation, and treatment of overweight and obesity in adults: the evidence report, NIH Publication No. 98-4083, September 1998). Yet, the available pharmacological therapies to facilitate weight loss fail to provide adequate benefit to many obese patients because of side effects, contraindications or lack of positive response (NIH Publication No. 98-4083, supra). Hence, there is impetus for developing new and alternative treatments for management of body weight, percentage body fat, and obesity.

Type II diabetes is brought on by a combination of genetic and acquired risk factors, including obesity, high-fat diet, lack of exercise, and aging. Worldwide, Type II diabetes has become an epidemic, driven by increases in obesity and a sedentary lifestyle, widespread adoption of western dietary habits, and the general aging of the population in many countries. In 1985, an estimated 30 million people worldwide had diabetes. By 2000, this FIGURE had increased 5-fold, to an estimated 154 million people. The number of people with diabetes is expected to double between now and 2025, to about 300 million.

Type II diabetes is characterized by defects in glucose and lipid metabolism. Typically there are perturbations in many metabolic parameters including increases in fasting plasma glucose levels, free fatty acid levels and triglyceride levels, as well as a decrease in the ratio of HDL/LDL. One of the principal underlying causes of diabetes is thought to be an increase in percentage body fat and insulin resistance in peripheral tissues, principally muscle and fat. What is needed is a method for treating excess weight, unwanted gain and increased body fat. Surprisingly, the present invention meets this and other needs.

BRIEF SUMMARY OF THE INVENTION

The invention provides methods for reducing body weight, reducing percentage body fat, treating obesity, facilitating or promoting weight loss, facilitating or promoting maintenance of a desired weight, and preventing or decreasing undesired weight gain. The present invention is also useful for treating disorders associated with obesity and higher than normal percentage body fat, such as type II diabetes, glucose intolerance, coronary artery disease, high blood pressure, and atherosclerosis.

In some embodiments, the present invention provides a method for reducing the body weight of a subject in need thereof, comprising administering to the subject a therapeutically effective amount of a compound of Formula I:

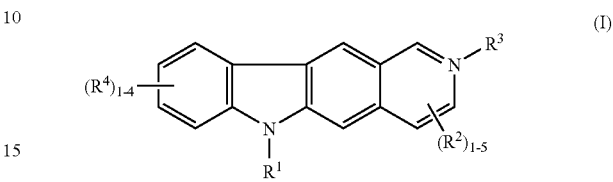

In Formula I, $R^1$ is H, $C_{1-6}$ alkyl, or $C_{1-6}$ alkyl-aryl. Each of $R^2$ and $R^4$ of Formula I are independently H, halogen, $C_{1-6}$ alkyl, $C_{1-6}$ haloalkyl, $C_{2-6}$ alkenyl, $C_{2-6}$ alkynyl, $C_{1-6}$ haloalkoxy, $-OR^{2a}$, $-SR^{2a}$, $-C(O)R^{2a}$, $-C(O)OR^{2a}$, $-C(O)NR^{2a}R^{2b}$, $-NR^{2a}R^{2b}$, $C_{1-6}$ alkyl-$NR^{2a}R^{2b}$, $-N(R^{2a})C(O)R^{2b}$, $-N(R^{2a})C(O)OR^{2b}$, $-N(R^{2a})C(O)NR^{2a}R^{2b}$, $-OP(O)(OR^{2a})_2$, $-S(O)_2OR^{2a}$, $-S(O)_2NR^{2a}R^{2b}$, $-CN$, $-NO_2$, cycloalkyl, heterocycloalkyl, aryl or heteroaryl. Each of $R^{2a}$ and $R^{2b}$ of Formula I are independently H, $C_{1-6}$ alkyl, $C_{1-10}$ heteroalkyl or $C_{1-6}$ alkyl-aryl. $R^3$ of Formula I is absent, $C_{1-6}$ alkyl or N-oxide. The compounds include the salts, hydrates and isomers thereof.

BRIEF DESCRIPTION OF THE DRAWINGS

FIG. 1 illustrates the results of the experiment described in Example 1. Seven groups of age and weight matched mice were subjected to the indicated conditions. Ellipticine hydrochloride was administered in three different doses (High, Mid, Low), and the results compared to those for Saline (negative control) and positive controls as described. The graph indicates the average weight loss for each group (grams). Even at the lowest dose, ellipticine hydrochloride decreased the body weight of mice by more than 18% over 4 weeks.

DETAILED DESCRIPTION OF THE INVENTION

I. General

The present invention encompasses compounds, compositions and methods for reducing body weight in a subject. The compounds of the present invention are SOST (Sclerostin) and Wise antagonists that modulate the Wnt pathway. By modulating the Wnt pathway, the compounds and compositions of the present invention reduce body weight, in particular, by reducing the amount of adipose tissue. The present invention thus provides compositions and modes of administration for delivering the compounds of the invention. The compounds and compositions of the present invention also can be used to prevent or treat obesity and/or obesity related disorders.

II. DEFINITIONS

As used herein, the term "pharmaceutically acceptable excipient" refers to a substance that aids the administration of an active agent to and absorption by a subject. Pharmaceutically acceptable excipients useful in the present invention include, but are not limited to, binders, fillers, disintegrants, lubricants, coatings, sweeteners, flavors and colors. One of skill in the art will recognize that other pharmaceutical excipients are useful in the present invention.

As used herein, the term "alkyl" refers to a straight or branched, saturated, aliphatic radical having the number of carbon atoms indicated. For example, $C_1$-$C_6$ alkyl includes, but is not limited to, methyl, ethyl, propyl, butyl, pentyl, hexyl, iso-propyl, iso-butyl, sec-butyl, tert-butyl, etc.

Alkylene represents either straight chain or branched alkylene of 1 to 7 carbon atoms, i.e. a divalent hydrocarbon radical of 1 to 7 carbon atoms; for instance, straight chain alkylene being the bivalent radical of Formula —$(CH_2)_n$—, where n is 1, 2, 3, 4, 5, 6 or 7. Preferably alkylene represents straight chain alkylene of 1 to 4 carbon atoms, e.g. a methylene, ethylene, propylene or butylene chain, or the methylene, ethylene, propylene or butylene chain mono-substituted by $C_1$-$C_3$-alkyl (preferably methyl) or disubstituted on the same or different carbon atoms by $C_1$-$C_3$-alkyl (preferably methyl), the total number of carbon atoms being up to and including 7. One of skill in the art will appreciate that a single carbon of the alkylene can be divalent, such as in —$CH((CH_2)_nCH_3)$—, wherein n=0-5.

As used herein, the term "alkoxy" refers to alkyl with the inclusion of an oxygen atom, for example, methoxy, ethoxy, etc. "Haloalkoxy" is as defined for alkoxy where some or all of the hydrogen atoms are substituted with halogen atoms. For example, halo-substituted-alkoxy includes trifluoromethoxy, etc.

As used herein, the team "alkenyl" refers to either a straight chain or branched hydrocarbon of 2 to 6 carbon atoms, having at least one double bond. Examples of alkenyl groups include, but are not limited to, vinyl, propenyl, isopropenyl, butenyl, isobutenyl, butadienyl, pentenyl or hexadienyl.

As used herein, the term "alkyl-aryl" refers to a radical having an alkyl component and a aryl component, where the alkyl component links the aryl component to the point of attachment. The alkyl component is as defined above, except that the alkyl component is at least divalent in order to link to the aryl component and to the point of attachment. In some instances, the alkyl component can be absent. The aryl component is as defined below. Examples of alkyl-aryl include benzyl, among others.

As used herein, the term "alkynyl" refers to either a straight chain or branched hydrocarbon of 2 to 6 carbon atoms, having at least one triple bond. Examples of alkynyl groups include, but are not limited to, acetylenyl, propynyl or butynyl.

As used herein, the term "halogen" refers to fluorine, chlorine, bromine and iodine.

As used herein, the term "haloalkyl" refers to alkyl as defined above where some or all of the hydrogen atoms are substituted with halogen atoms. Halogen (halo) preferably represents chloro or fluoro, but may also be bromo or iodo. For example, haloalkyl includes trifluoromethyl, fluoromethyl, 1,2,3,4,5-pentafluoro-phenyl, etc. The term "perfluoro" defines a compound or radical which has at least two available hydrogens substituted with fluorine. For example, perfluorophenyl refers to 1,2,3,4,5-pentafluorophenyl, perfluoromethane refers to 1,1,1-trifluoromethyl, and perfluoromethoxy refers to 1,1,1-trifluoromethoxy.

As used herein, the term "heteroalkyl" refers to an alkyl group having from 1 to 3 heteroatoms such as N, O and S. Additional heteroatoms can also be useful, including, but not limited to, B, Al, Si and P. The heteroatoms can also be oxidized, such as, but not limited to, —S(O)— and —S(O)$_2$—. For example, heteroalkyl can include ethers, thioethers and alkyl-amines.

As used herein, the term "hydroxyalkyl" refers to alkyl as defined above where at least one of the hydrogen atoms is substituted with a hydroxy group. For example, hydroxyalkyl includes hydroxy-methyl, hydroxy-ethyl (1- or 2-), hydroxy-propyl (1-, 2- or 3-), hydroxy-butyl (1-, 2-, 3- or 4-), hydroxy-pentyl (1-, 2-, 3-, 4- or 5-), hydroxy-hexyl (1-, 2-, 3-, 4-, 5- or 6-), 1,2-dihydroxyethyl, and the like. One of skill in the art will appreciate that other hydroxyalkyl groups are useful in the present invention.

As used herein, the term "cycloalkyl" refers to a saturated or partially unsaturated, monocyclic, fused bicyclic or bridged polycyclic ring assembly containing from 3 to 12 ring atoms, or the number of atoms indicated For example, $C_{3-8}$cycloalkyl includes cyclopropyl, cyclobutyl, cyclopentyl, cyclohexyl, and up to cyclooctyl.

As used herein, the term "heterocycloalkyl" refers to a ring system having from 3 ring members to about 20 ring members and from 1 to about 5 heteroatoms such as N, O and S. Additional heteroatoms can also be useful, including, but not limited to, B, Al, Si and P. The heteroatoms can also be oxidized, such as, but not limited to, —S(O) — and —S(O)$_2$—. For example, heterocycloalkyl includes, but is not limited to, tetrahydrofuranyl, tetrahydrothiophenyl, morpholino, pyrrolidinyl, pyrrolinyl, imidazolidinyl, imidazolinyl, pyrazolidinyl, pyrazolinyl, piperazinyl, piperidinyl, indolinyl, quinuclidinyl and 1,4-dioxa-8-aza-spiro[4.5]dec-8-yl.

As used herein, the term "aryl" refers to a monocyclic or fused bicyclic, tricyclic or greater, aromatic ring assembly containing 6 to 16 ring carbon atoms. For example, aryl may be phenyl, benzyl or naphthyl, preferably phenyl. "Arylene" means a divalent radical derived from an aryl group. Aryl groups can be mono-, di- or tri-substituted by one, two or three radicals selected from alkyl, alkoxy, aryl, hydroxy, halogen, cyano, amino, amino-alkyl, trifluoromethyl, alkylenedioxy and oxy-$C_2$-$C_3$-alkylene; all of which are optionally further substituted, for instance as hereinbefore defined; or 1- or 2-naphthyl; or 1- or 2-phenanthrenyl. Alkylenedioxy is a divalent substitute attached to two adjacent carbon atoms of phenyl, e.g. methylenedioxy or ethylenedioxy. Oxy-$C_2$-$C_3$-alkylene is also a divalent substituent attached to two adjacent carbon atoms of phenyl, e.g. oxyethylene or oxypropylene. An example for oxy-$C_2$-$C_3$-alkylene-phenyl is 2,3-dihydrobenzofuran-5-yl.

Preferred as aryl is naphthyl, phenyl or phenyl mono- or disubstituted by alkoxy, phenyl, halogen, alkyl or trifluoromethyl, especially phenyl or phenyl-mono- or disubstituted by alkoxy, halogen or trifluoromethyl, and in particular phenyl.

Examples of substituted phenyl groups as R are, e.g. 4-chlorophen-1-yl, 3,4-dichlorophen-1-yl, 4-methoxyphen-1-yl, 4-methylphen-1-yl, 4-aminomethylphen-1-yl, 4-methoxyethylaminomethylphen-1-yl, 4-hydroxyethylaminomethylphen-1-yl, 4-hydroxyethyl-(methyl)-aminomethylphen-1-yl, 3-aminomethylphen-1-yl, 4-N-acetylaminomethylphen-1-yl, 4-aminophen-1-yl, 3-aminophen-1-yl, 2-aminophen-1-yl, 4-phenyl-phen-1-yl, 4-(imidazol-1-yl)-phen-yl, 4-(imidazol-1-ylmethyl)-phen-1-yl, 4-(morpholin-1-yl)-phen-1-yl, 4-(morpholin-1-ylmethyl-phen-1-yl, 4-(2-methoxyethylaminomethyl)-phen-1-yl and 4-(pyrrolidin-1-ylmethyl)-phen-1-yl, 4-(thiophenyl)-phen-1-yl, 4-(3-thiophenyl)-phen-1-yl, 4-(4-methylpiperazin-1-yl)-phen-1-yl, and 4-(piperidinyl)-phenyl and 4-(pyridinyl)-phenyl optionally substituted in the heterocyclic ring.

As used herein, the term "heteroaryl" refers to a monocyclic or fused bicyclic or tricyclic aromatic ring assembly containing 5 to 16 ring atoms, where from 1 to 4 of the ring atoms are a heteroatom each N, O or S. For example, heteroaryl includes pyridyl, indolyl, indazolyl, quinoxalinyl, quinolinyl, isoquinolinyl, benzothienyl, benzofuranyl, furanyl, pyrrolyl, thiazolyl, benzothiazolyl, oxazolyl, isoxazolyl, triazolyl, tetrazolyl, pyrazolyl, imidazolyl, thienyl, or any other radicals substituted, especially mono- or di-substituted, by e.g. alkyl, nitro or halogen. Pyridyl represents 2-, 3- or 4-pyridyl, advantageously 2- or 3-pyridyl. Thienyl represents 2- or 3-thienyl. Quinolinyl represents preferably 2-, 3- or 4-quinolinyl. Isoquinolinyl represents preferably 1-, 3- or 4-isoquinolinyl. Benzopyranyl, benzothiopyranyl represents preferably 3-benzopyranyl or 3-benzothiopyranyl, respectively. Thiazolyl represents preferably 2- or 4-thiazolyl, and most preferred, 4-thiazolyl. Triazolyl is preferably 1-, 2- or 5-(1,2,4-triazolyl). Tetrazolyl is preferably 5-tetrazolyl.

Preferably, heteroaryl is pyridyl, indolyl, quinolinyl, pyrrolyl, thiazolyl, isoxazolyl, triazolyl, tetrazolyl, pyrazolyl, imidazolyl, thienyl, furanyl, benzothiazolyl, benzofuranyl, isoquinolinyl, benzothienyl, oxazolyl, indazolyl, or any of the radicals substituted, especially mono- or di-substituted.

Substituents for the aryl and heteroaryl groups are varied and are selected from: -halogen, —OR', —OC(O)R', —NR'R", —SR', —R', —CN, —NO$_2$, —CO$_2$R', —CONR'R", —C(O)R', —OC(O)NR'R", —NR"C(O)R', —NR"C(O)$_2$R', —NR'—C(O)NR"R''', —NH—C(NH$_2$)=NH, —NR'C(NH$_2$)=NH, —NH—C(NH$_2$)=NR', —S(O)R', —S(O)$_2$R', —S(O)$_2$NR"R", —N$_3$, —CH(Ph)$_2$, perfluoro (C$_1$-C$_4$)alkoxy, and perfluoro(C$_1$-C$_4$)alkyl, in a number ranging from zero to the total number of open valences on the aromatic ring system; and where R', R" and R''' are independently selected from hydrogen, (C$_1$-C$_8$)alkyl and heteroalkyl, unsubstituted aryl and heteroaryl, (unsubstituted aryl)-(C$_1$-C$_4$)alkyl, and (unsubstituted aryl)oxy-(C$_1$-C$_4$)alkyl.

Two of the substituents on adjacent atoms of the aryl or heteroaryl ring may optionally be replaced with a substituent of the formula -T-C(O)—(CH$_2$)$_q$—U—, wherein T and U are independently —NH—, —O—, —CH$_2$— or a single bond, and q is an integer of from 0 to 2. Alternatively, two of the substituents on adjacent atoms of the aryl or heteroaryl ring may optionally be replaced with a substituent of the formula -A-(CH$_2$)$_r$—B—, wherein A and B are independently —CH$_2$—, —O—, —NH—, —S—, —S(O)—, —S(O)$_2$—, —S(O)$_2$NR'— or a single bond, and r is an integer of from 1 to 3. One of the single bonds of the new ring so formed may optionally be replaced with a double bond. Alternatively, two of the substituents on adjacent atoms of the aryl or heteroaryl ring may optionally be replaced with a substituent of the formula —(CH$_2$)$_s$—X—(CH$_2$)$_t$—, where s and t are independently integers of from 0 to 3, and X is —O—, —NR'—, —S—, —S(O)—, —S(O)$_2$—, or —S(O)$_2$NR'—. The substituent R' in —NR'— and —S(O)$_2$NR'— is selected from hydrogen or unsubstituted (C$_1$-C$_6$)alkyl.

As used herein, the term "salt" refers to acid or base salts of the compounds used in the methods of the present invention. Illustrative examples of pharmaceutically acceptable salts are mineral acid (hydrochloric acid, hydrobromic acid, phosphoric acid, and the like) salts, organic acid (acetic acid, propionic acid, glutamic acid, citric acid and the like) salts, quaternary ammonium (methyl iodide, ethyl iodide, and the like) salts. It is understood that the pharmaceutically acceptable salts are non-toxic. Additional information on suitable pharmaceutically acceptable salts can be found in *Remington's Pharmaceutical Sciences*, 17th ed., Mack Publishing Company, Easton, Pa., 1985, which is incorporated herein by reference.

Pharmaceutically acceptable salts of the acidic compounds of the present invention are salts formed with bases, namely cationic salts such as alkali and alkaline earth metal salts, such as sodium, lithium, potassium, calcium, magnesium, as well as ammonium salts, such as ammonium, trimethyl-ammonium, diethylammonium, and tris-(hydroxymethyl)-methyl-ammonium salts.

Similarly acid addition salts, such as of mineral acids, organic carboxylic and organic sulfonic acids, e.g., hydrochloric acid, methanesulfonic acid, maleic acid, are also possible provided a basic group, such as pyridyl, constitutes part of the structure.

The neutral forms of the compounds can be regenerated by contacting the salt with a base or acid and isolating the parent compound in the conventional manner. The parent form of the compound differs from the various salt forms in certain physical properties, such as solubility in polar solvents, but otherwise the salts are equivalent to the parent form of the compound for the purposes of the present invention.

As used herein, the term "hydrate" refers to a compound that is complexed to at least one water molecule. The compounds of the present invention can be complexed with from 1 to 10 water molecules.

Certain compounds of the present invention possess asymmetric carbon atoms (optical centers) or double bonds; the racemates, diastereomers, geometric isomers and individual isomers are all intended to be encompassed within the scope of the present invention.

As used herein, the term "subject" refers to a human or non-human animal including, but not limited to, primates, dogs, cats, cows, sheep, goats, horses, dogs, cats, rabbits, rats, mice and the like.

As used herein, the terms "therapeutically effective amount or dose" or "therapeutically sufficient amount or dose" or "effective or sufficient amount or dose" refer to a dose that produces the effects for which it is administered. The exact dose will depend on the purpose of the treatment, e.g., reducing body weight, reducing adipose tissue, treating type II diabetes and/or obesity, and the individual characteristics of the subject. Common dose determining techniques are disclosed, e.g., in Lieberman, *Pharmaceutical Dosage Forms* (vols. 1-3, 1992); Lloyd, *The Art, Science and Technology of Pharmaceutical Compounding* (1999); Pickar, *Dosage Calculations* (1999); and *Remington: The Science and Practice of Pharmacy*, 20th Edition, 2003, Gennaro, Ed., Lippincott, Williams & Wilkins.

In some embodiments, a therapeutically effective dose refers to the amount sufficient to reduce body weight by 1%, 2%, 3%, 4%, 5%, 10%, 15%, 20%, 25%, 30%, 40%, 50%, or more, as compared to the body weight of the individual before treatment or to the body weight of a control individual with a similar health profile not undergoing treatment. In some embodiments, a therapeutically effective dose refers to the amount sufficient to reduce percentage body fat by 1%, 2%, 3%, 4%, 5%, 10%, 15%, 20%, 25%, 30%, 40%, 50%, or more, as compared to the percentage of the individual before treatment or to the percentage of a control individual with a similar health profile not undergoing treatment. In some embodiments, a therapeutically effective dose reduces the risk factors of an individual for developing type II diabetes, e.g., as measured by glucose and/or insulin regulation. In some embodiments, a therapeutically effective dose reduces the severity of diabetes symptoms, e.g., by reducing the frequency or severity of hypoglycemic and/or hyperglycemic episodes. Any reduction in the severity of such symptoms, as compared to the individual before treatment or to a control individual with a similar health profile not undergoing treatment, is envisioned as part of the present invention.

As used herein, "administering" means oral ("po") administration, administration as a suppository, topical contact, intravenous ("iv"), intraperitoneal ("ip"), intramuscular ("im"), intralesional, intranasal or subcutaneous ("sc") administration, or the implantation of a slow-release device e.g., a mini-osmotic pump, to an individual. Administration can be by any route including parenteral and transmucosal (e.g., oral, nasal, vaginal, rectal, or transdermal). Parenteral administration includes, e.g., intravenous, intramuscular, intra-arteriole, intradermal, subcutaneous, intraperitoneal, intraventricular, and intracranial. Other modes of delivery include, but are not limited to, the use of liposomal formulations, intravenous infusion, transdermal patches, etc.

As used herein, the terms "treat", "treating" and "treatment" refers to any indicia of success in the treatment or amelioration of a condition or symptom (e.g., percentage body fat, glucose tolerance, BMI, insulin levels), including any objective or subjective parameter such as abatement; remission; diminishing of symptoms or making the symptom, injury, pathology or condition more tolerable to the patient; decreasing the frequency or duration of the symptom or condition; or, in some situations, delaying or preventing the onset of the symptom or condition. The treatment or amelioration of symptoms can be based on any objective or subjective parameter including, e.g., standard results from a physical examination.

As used here, the term "co-administer" refers to the administration of at least two active agents to individual. Active agents that are co-administered can be concurrently or sequentially delivered.

As used herein, the term "reducing the body weight" refers to reduction of the body weight of an individual compared to a baseline body weight, measured, e.g., before therapy. Alternatively, weight reduction can be determined relative to a control individual with a similar health profile that does not receive treatment. The term also refers to reduction of percentage body fat in an individual. In some embodiments, the present invention preferentially reduces fat mass as compared to lean mass. Reduction of body weight also refers to a reduced rate of increase in body weight, such as in the case of an individual that is still growing, so that the growth rate of the individual is within a normal range for the age of the individual.

As used herein, the term "obese" or "obesity" refers to an individual who has a body mass index (BMI) of 30 kg/m$^2$ or more due to excess adipose tissue. According to the World Health Organization, obesity is defined as a Body Mass Index (BMI) greater than 27.8 kg/m$^2$ for men and 27.3 kg/m$^2$ for women. A "morbidly obese" individual has a body mass index greater than 35 kg/m$^2$. Obesity also can be defined on the basis of body fat content or percentage body fat. Obesity is generally defined as greater than 25% body fat for a male or more than 30% body fat content for a female. Obesity is linked to a variety of medical conditions including diabetes and hyperlipidemia.

As used herein, the term "overweight" refers to an individual who has a body mass index of 25 kg/m$^2$ or more, but less than 30 kg/m$^2$. The term "body mass index" or "BMI" refers to a weight to height ratio measurement that estimates whether an individual's weight is appropriate for their height. As used herein, an individual's body mass index can be calculated as follows:

BMI=(pounds×703)/(height in inches)$^2$ or

BMI=(kilograms)/(height in meters)$^2$

As used herein, the term "baseline body weight" refers to the body weight presented by the individual at the initiation of treatment.

As used herein, the term "non-obese" and "lean" are used synonymously herein. Non-obese individuals have a BMI and/or percentage body fat that is within recommended levels or close to recommended levels (also referred to as "normal" levels). Recommended BMI ranges from about 18.5-25. Recommended percentage body fat is generally 20-25% for women and 8-14% for men. Athletes can have lower percentages. According to some measures, levels as high as 25-30% for women and 18-25% for men are acceptable. Alternatively, a "lean individual" can refer to an adult with a fasting blood glucose level less than 110 mg/dl or a 2 hour prandial glucose (PG) reading of 140 mg/dl. "Fasting" refers to no caloric intake for at least 8 hours. A "2 hour PG" refers to the level of blood glucose after challenging a patient to a glucose load containing the equivalent of 75 g anhydrous glucose dissolved in water. The overall test is generally referred to as an oral glucose tolerance test (OGTT) (see, e.g., *Diabetes Care, Supplement* 2002, American Diabetes Association: Clinical Practice Recommendations 2002). The level of a polypeptide in a lean individual can be a reading from a single individual, but is typically a statistically relevant average from a group of lean individuals. The level of a polypeptide in a lean individual can be represented by a value, for example in a computer program.

As used herein, the term "diabetes mellitus" or "diabetes" means a disease or condition that is generally characterized by metabolic defects in production and utilization of glucose which result in the failure to maintain appropriate blood sugar levels in the body. The result of these defects is elevated blood glucose, referred to as "hyperglycemia." Two major forms of diabetes are Type 1 diabetes and Type 2 diabetes. Type 2 (or type II) diabetes often occurs in the face of normal, or even elevated levels of insulin and can result from the inability of tissues to respond appropriately to insulin. Most Type 2 diabetic patients are insulin resistant and have a relative deficiency of insulin, in that insulin secretion cannot compensate for the resistance of peripheral tissues to respond to insulin. Obesity and/or a higher than normal percentage body fat is a major risk factor for development of type 2 diabetes (see, e.g., Barrett-Conner, E., *Epidemol. Rev.* (1989) 11: 172-181; and Knowler, et al., *Am. J. Clin. Nutr.* (1991) 53:1543-1551).

As used herein, the term "pre-diabetic individual," when used to compare with a sample from a patient, refers to an adult with a fasting blood glucose level greater than 110 mg/dl but less than 126 mg/dl or a 2 hour PG reading of greater than 140 mg/dl but less than 200 mg/dl. A "diabetic individual," when used to compare with a sample from a patient, refers to an adult with a fasting blood glucose level greater than 126 mg/dl or a 2 hour PG reading of greater than 200 mg/dl.

As used herein, the term "predisposition for diabetes" refers to a person having a high risk for developing diabetes. A number of risk factors are known to those of skill in the art and include: genetic factors; being overweight; habitual physical inactivity; race/ethnicity; impaired fasting glucose or impaired glucose tolerance; hypertension (e.g., greater or equal to 140/90 mmHg in adults); HDL cholesterol greater or equal to 35 mg/dl; triglyceride levels greater or equal to 250 mg/dl; a history of gestational diabetes or delivery of a baby over nine pounds; and/or polycystic ovary syndrome. See, e.g., "Report of the Expert Committee on the Diagnosis and Classification of Diabetes Mellitus" and "Screening for Diabetes" *Diabetes Care* 25(1): S5-S24 (2002).

As used herein, the term "insulin sensitivity" refers to the effect of insulin on glucose uptake in a cell. Sensitivity can be determined at an organismal, tissue or cellular level. For example, blood or urine glucose levels following a glucose tolerance test are indicative of insulin sensitivity. Other methods of measuring insulin sensitivity include, e.g., measuring glucose uptake (see, e.g., Garcia de Herreros, A., and Birnbaum, M. J. *J. Biol. Chem.* 264, 19994-19999 (1989); Klip, A., Li, G., and Logan, W. J. *Am. J. Physiol.* 247, E291-296 (1984)), measuring the glucose infusion rate (GINF) into tissue such as the skeletal muscle (see, e.g., Ludvik et al., *J. Clin. Invest.* 100:2354 (1997); Frias et al., *Diabetes Care* 23:64, (2000)) and measuring sensitivity of GLUT4 translocation (e.g., as described herein) in response to insulin.

As used herein, the term "anti-obesity agent" or "drug for treatment of obesity" refers to a pharmaceutical agent whose primary purpose is to effect weight loss. Exemplary anti-obesity agents include, without limitation, anorexiants, dopamine agonists, $H_3$-histamine antagonists, 5-HT2c receptor agonists, beta-3 adrenergic receptor agonists, cholecystokinin agonists, anti-epileptic agents, leptin, leptin analogs and leptin receptor agonists, neuropeptide Y (NPY) receptor antagonists and modulators, peptide-YY (PYY) receptor agonists, ciliary neurotrophic factor, thyroid hormone receptor-beta agonists, cannabinoid CB1 receptor antagonists, melanin-concentrating hormone receptor antagonists, pancreatic and gastric lipase inhibitors, melanocortin-4 receptor agonists, and combinations thereof.

Anti-obesity therapies include the anti-obesity agents described above, as well as non-pharmaceutical approaches. For example, anti-obesity therapies can include dietary counseling, reduction of caloric intake, increased physical activity, as well as surgical approaches, including gastric bypass and liposuction.

III. Compounds

The compounds useful in the methods of the present invention include any ellipticine derivative. In some embodiments, the compounds of the present invention have Formula I:

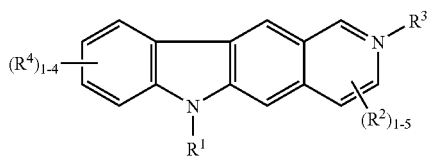

(I)

In Formula I, $R^1$ is H, $C_{1-6}$ alkyl, or $C_{1-6}$ alkyl-aryl. Each of $R^2$ and $R^4$ of Formula I are independently H, halogen, $C_{1-6}$ alkyl, $C_{1-6}$ haloalkyl, $C_{2-6}$ alkenyl, $C_{2-6}$ alkynyl, $C_{1-6}$ haloalkoxy, —$OR^{2a}$, —$SR^{2a}$, —$C(O)R^{2a}$, —$C(O)OR^{2a}$, —$C(O)NR^{2a}R^{2b}$, —$NR^{2a}R^{2b}$, $C_{1-6}$ alkyl-$NR^{2a}R^{2b}$, —$N(R^{2a})C(O)R^{2b}$, —$N(R^{2a})C(O)OR^{2b}$, —$N(R^{2a})C(O)NR^{2a}R^{2b}$, —$OP(O)(OR^{2a})_2$, —$S(O)_2OR^{2a}$, —$S(O)_2NR^{2a}R^{2b}$, —CN, —$NO_2$, cycloalkyl, heterocycloalkyl, aryl or heteroaryl. Each of $R^{2a}$ and $R^{2b}$ of Formula I are independently H, $C_{1-6}$ alkyl, $C_{1-10}$ heteroalkyl or $C_{1-6}$ alkyl-aryl. $R^3$ of Formula I is absent, $C_{1-6}$ alkyl or N-oxide. The compounds include the salts, hydrates and isomers thereof.

In some embodiments, $R^2$ of Formula I is $C_{1-6}$ alkyl, —$NR^{2a}R^{2b}$ or heterocycloalkyl, each of $R^{2a}$ and $R^{2b}$ are $C_{1-10}$ heteroalkyl, and $R^3$ of Formula I is absent. In another embodiment, $R^2$ is $C_{1-6}$ alkyl and $R^3$ is absent. In some other embodiments, the compound is the salt form. In still other embodiments, the compound is the hydrochloride salt.

In other embodiments, the compound has the following formula:

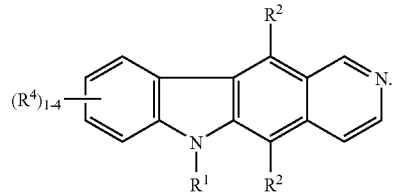

In some other embodiments, the compound has the following formula:

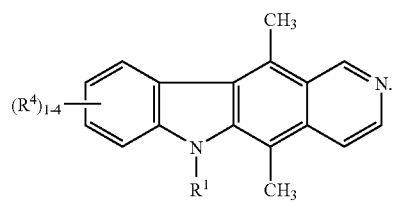

In still other embodiments, the compound has the following formula:

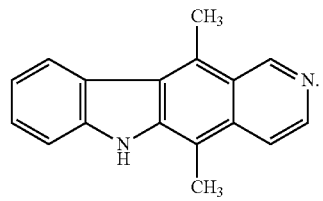

In yet other embodiments, the compound is the hydrochloride salt.

Compounds of Formula I useful in the methods of the present invention are described in the table below.

TABLE I

Compounds of Formula I.

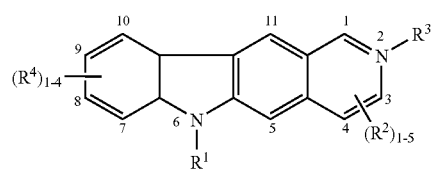

(I)

| Compound | $R^1$ | $R^2$ | $R^3$ | $R^4$ |
|---|---|---|---|---|
| 1 | H | H | — | H |
| 2 | H | 1-Me, 5-Me | — | H |
| 3 | H | 5-Me | — | H |
| 4 | H | 5-Me, 11-Me | — | 8-OMe |
| 5 | H | 5-Me, 11-Me | — | 9-OMe |
| 6 | H | 1-Me, 5-Me | — | 9-OMe |
| 7 | H | 5-Me, 11-Me | — | 9-Me |
| 8 | Me | 5-Me, 11-Me | — | 9-OMe |
| 9 | Me | 5-Me, 11-Me | — | H |
| 10 | H | 5-Me, 11-Me | — | 9-Br |
| 11 | H | 5-Me, 11-Me | — | 9-$NO_2$ |
| 12 | H | 5-Me, 11-Me | — | H |
| 13 | H | 5-Me, 11-Me | —$O^-$ | H |
| 14 | H | 5-Me, 11-Me | — | 9-OH |
| 15 | —$(CH_2)_2CH(CH_3)_2$ | 5-Me, 11-Me | — | 9-OMe |

TABLE I-continued

Compounds of Formula I.

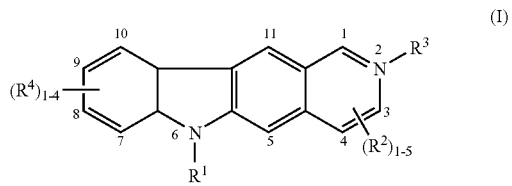

(I)

| Compound | R¹ | R² | R³ | R⁴ |
|---|---|---|---|---|
| 16 | H | 5-Me, 11-Me | — | 9-NH$_2$ |
| 17 | —(CH$_2$)$_2$CH(CH$_3$)$_2$ | 5-Me, 11-Me | — | H |
| 18 | Me | 5-Me, 11-Me | — | 9-OH |
| 19 | H | 11-Me | — | 9-OMe |
| 20 | H | 5-Me, 11-Me | — | 7-OMe |
| 21 | Me | 5-Me, 11-Me | Me | 9-OH |
| 22 | H | 5-Me, 11-Me | Me | H |
| 23 | H | 5-Me, 11-Me | — | 9-F |
| 24 | H | 1-Me, 5-Me | — | 9-OH |
| 25 | H | 5-Me, 11-Me | Me | 9-OMe |
| 26 | H | 5-Me, 11-Me | Et | 9-OH |
| 27 | H | 1-Cl, 5-Me, 11-Me | — | 9-OMe |
| 28 | H | 1-NH(CH$_2$)$_3$N(Et)$_2$, 5-Me | — | 9-OMe |
| 29 | H | 1-NH(CH$_2$)$_3$N(Et)$_2$, 5-Me | — | 9-OBz |
| 30 | H | 1-NH(CH$_2$)$_3$N(Et)$_2$, 5-Me, 11-Me | — | 9-OMe |
| 31 | H | 1-NH(CH$_2$)$_3$N(Et)$_2$, 5-Me, 11-Me | — | 9-OBz |
| 32 | H | 1-NH(CH$_2$)$_3$N(Et)$_2$, 5-Me | — | 9-OH |
| 33 | H | 1-NH(CH$_2$)$_3$N(Et)$_2$, 5-Me, 11-Me | — | 9-OH |
| 34 | H | 1-NH(CH$_2$)$_2$NH$_2$, 5-Me | — | 9-OMe |
| 35 | H | 1-NH(CH$_2$)$_3$NH$_2$, 5-Me | — | 9-OMe |
| 36 | H | 1-NH(CH$_2$)$_4$NH$_2$, 5-Me | — | 9-OMe |
| 37 | H | 1-NH(CH$_2$)$_2$CH(Et)NH$_2$, 5-Me | — | 9-OMe |
| 38 | H | 1-NH(CH$_2$)$_6$NH$_2$, 5-Me | — | 9-OMe |
| 39 | H | 1-NH(CH$_2$)$_2$N(Me)$_2$, 5-Me | — | 9-OMe |
| 40 | H | 1-NH(CH$_2$)$_3$N(Me)$_2$, 5-Me, 11-Me | — | 9-OMe |
| 41 | H | 1-NH(CH$_2$)$_2$N(Me)$_2$, 5-Me | — | 9-OBz |
| 42 | H | 1-NH(CH$_2$)$_2$N(Me)$_2$, 5-Me | — | 9-OH |
| 43 | H | 1-piperidin-1-yl, 5-Me | — | 9-OMe |
| 44 | H | 5-C(O)H, 11-Me | — | H |
| 45 | H | 5-Me, 11-Me | — | 7-Cl, 9-Cl |
| 46 | H | 5-Me | — | 9-OH |
| 47 | H | 5-Me, 11-Me | — | 8-NO$_2$ |
| 48 | H | 5-Me, 11-Me | — | 10-OH |
| 49 | H | 1-Me, 5-Me | — | 7-OH |
| 50 | H | 5-C(O)H, 11-Me | —O⁻ | H |
| 51 | H | 5-Me, 11-CH$_2$OH | — | H |

The compounds of the present invention also include the salts, hydrates, solvates and prodrug forms. The compounds of the present invention also include the isomers and metabolites of those described in Formula I. Certain compounds of the present invention possess asymmetric carbon atoms (optical centers) or double bonds; the racemates, diastereomers, geometric isomers and individual isomers are all intended to be encompassed within the scope of the present invention. For example, the compound of the present invention can be the R-isomer or the S-isomer, or a mixture thereof. In addition, the compound of the present invention can be the E-isomer or the Z-isomer, or a combination thereof.

Pharmaceutically acceptable salts of the acidic compounds of the present invention are salts formed with bases, namely cationic salts such as alkali and alkaline earth metal salts, such as sodium, lithium, potassium, calcium, magnesium, as well as ammonium salts, such as ammonium, trimethyl-ammonium, diethylammonium, and tris-(hydroxymethyl)-methyl-ammonium salts. In some embodiments, the present invention provides the hydrochloride salt. In other embodiments, the compound is ellipticine hydrochloride.

Similarly acid addition salts, such as of mineral acids, organic carboxylic and organic sulfonic acids, e.g., hydrochloric acid, methanesulfonic acid, maleic acid, are also possible provided a basic group, such as pyridyl, constitutes part of the structure.

The neutral forms of the compounds can be regenerated by contacting the salt with a base or acid and isolating the parent compound in the conventional manner. The parent form of the compound differs from the various salt forms in certain physical properties, such as solubility in polar solvents, but otherwise the salts are equivalent to the parent form of the compound for the purposes of the present invention.

The compounds of the present invention can be made by a variety of methods known to one of skill in the art (see *Comprehensive Organic Transformations* Richard C. Larock, 1989). One of skill in the art will appreciate that other methods of making the compounds are useful in the present invention.

IV. Obesity and Related Disorders

The present methods and compositions find use in the treatment of weight-related disorders. Exemplary issues addressed by the present methods and compositions include, without limitation, obesity, undesired or excessive weight, higher than recommended percentage body fat, and disorders related to obesity and/or higher than recommended percentage body fat, such as diabetes, coronary artery disease, high blood pressure, atherosclerosis, and insulin resistance.

According to the World Health Organization, obesity is defined as a Body Mass Index (BMI) greater than 27.8 kg/m$^2$ for men and 27.3 kg/m$^2$ for women. According to some measures, however, obesity is only diagnosed with a BMI of 30 kg/m$^2$ or more. For example, a BMI between 25-29.9 is considered overweight by the National Institutes of Health (see National Heart Lung and Blood Institute: Clinical Guidelines on the Identification, Evaluation, and Treatment of Overweight and Obesity in Adults. June 1998). A "morbidly obese" individual has a body mass index greater than 35 kg/m$^2$. Obesity can also be defined on the basis of body fat content or percentage body fat. Obesity is generally defined as greater than 25% body fat for a male or more than 30% body fat content for a female.

Carrying excess body fat results in a number of undesirable effects. These can range from dissatisfaction with one's appearance, to type II diabetes, atherosclerosis, high blood pressure, heart disease, and any number of related disorders.

Diabetes mellitus can be divided into two clinical syndromes, Type I and Type II diabetes mellitus. Type I, or insulin-dependent diabetes mellitus (IDDM), is a chronic autoimmune disease characterized by the extensive loss of beta cells in the pancreatic Islets of Langerhans, which produce insulin. As these cells are progressively destroyed, the amount of secreted insulin decreases, eventually leading to hyperglycemia (abnormally high level of glucose in the blood) when the amount of secreted insulin drops below the level required for euglycemia (normal blood glucose level).

Type II diabetes (also referred to as type 2 or non-insulin dependent diabetes mellitus (NIDDM)) develops when muscle, fat and liver cells fail to respond normally to insulin. This failure to respond (called insulin resistance) may be due to reduced numbers of insulin receptors on these cells, or a dysfunction of signaling pathways within the cells, or both. The beta cells initially compensate for this insulin resistance by increasing insulin output. Over time, these cells become unable to produce enough insulin to maintain normal glucose levels, indicating progression to type II diabetes.

V. Methods of Treating Weight Gain

In some embodiments, the present invention provides a method for reducing the body weight of a subject in need thereof, by administering to the subject a therapeutically effective amount of a compound of the present invention.

The subject being treated by the methods of the present invention can be overweight and is not already being treated with a compound of the present invention. A subject can be overweight as defined by a BMI of 25 kg/m² or more. Other measures of overweight status or obesity are known to one of skill in the art. In some embodiments, the subject is not overweight, but experiencing unwanted weight gain. Unwanted weight gain can result from natural processes or treatment for an unrelated condition.

In other embodiments, the invention provides methods for reducing percentage body fat comprising administering to the subject in need thereof a therapeutically effective amount of a compound of the present invention, or a derivative thereof, thereby reducing percentage body fat in the subject.

In some embodiments, the method further comprises an additional anti-obesity therapy. In other embodiments, the anti-obesity therapy is a pharmaceutical. In some other embodiments, the anti-obesity therapy is non-pharmaceutical (e.g., reducing caloric intake, increasing physical activity, or surgical procedures)

In some embodiments, the present invention provides methods for preventing or treating type II diabetes in a subject in need thereof comprising administering to the subject a therapeutically effective amount of a compound of the present invention, or a derivative thereof, thereby preventing or treating type II diabetes in the individual. In other embodiments, the individual is pre-diabetic. In some other embodiments, the individual is at risk of developing type II diabetes. In still other embodiments, the method further comprises co-administration with an anti-diabetic agent.

VI. Assays to Diagnose or Monitor Obesity and Related Disorders

The present invention provides compositions and methods for reducing body weight, reducing percentage body fat, reducing BMI, treating or preventing obesity, and/or treating disorders related to higher than normal or recommended percentage body fat (e.g., type II diabetes). Methods of measuring these conditions, for purposes of comparison before and after treatment, are provided herein.

In some embodiments, the invention provides methods of screening a candidate SOST antagonist, for its ability to reduce body weight. In such methods, a candidate SOST antagonist is administered to a test animal, with a control animal receiving an equal volume of control solution without the SOST antagonist candidate. Administration can be according to any route described herein.

Animals that can be used for such purposes include models of obesity and/or diabetes. Several mouse models of obesity and/or diabetes are known and commercially available, e.g., from Jackson Laboratories (Bar Harbor, Me.). Obese models include: Apoe$^{tm1Unc}$ NONcNZO10/LtJ, SmJ, and C57BL/6J-hlb575. Obese, type II diabetes models include: NOD, ob/ob, Cpe$^{fat}$, and Tub$^{tub}$ mice. Diet-induced Type II diabetes models include AKR/J and Ldlr$^{tm1Her}$ mice, and (UcpDta) 1 Kz transgenic mice. Rat models for obesity are also commonly used and available, e.g., from Harlan Sprague Dawley. Such models include Zucker and Ob rats.

Relevant metrics can be measured in animal models to determine the efficacy of a candidate compound of the present invention. For example, a candidate compound can be administered to an animal model for obesity and the body weight and percentage body fat monitored over time. Relevant controls can include no administration, vehicle, or saline administration, administration of a wild type (non-obese or diabetic) animal, and/or administration of a compound with known efficacy.

Similarly, individuals undergoing treatment can be monitored over time for relevant metrics, as described below.

Generally, determination of body weight, percentage body fat, and related conditions can be accomplished in a simple physical examination of the individual. For example, the following assessments can be performed: weight; height; circumference of waist, upper arm, hips, and wrist; blood pressure; heart rate; and dietary compliance (e.g., if a particular diet is recommended in combination with treatment). Blood chemistry can be assessed, e.g., for creatinine, glucose, triglycerides, high and low density lipoproteins.

Creatinine levels can increase as a result of reduced kidney function associated with diabetes. Triglyceride levels are also frequently elevated from a normal fasting level of 150 mg/dL. Triglycerides are believed to block leptin function and result in obesity. Reduced HDL levels and elevated LDL (especially small LDL) levels are associated with obesity.

BMI can be calculated using any number of available on-line calculators. While not the most accurate indication of body fat, the test is easy, inexpensive, and correlates well with direct measurements such as underwater testing and dual emission x-ray absorptiometry (DEXA). The Centers for Disease Control and Prevention publishes guidelines for acceptable and recommended BMI. BMI can be calculated as kg body weight/height in meters squared (or 703*pounds body weight/height in inches squared). Normal BMI is 18.5-24.9 for adults. The calculation is more complicated for children and teens, as it depends on age and stage of growth relative to the individual's age cohort.

Direct measures of body fat include skinfold tests (e.g., back of upper arm and gut), underwater (hydrostatic) testing, DEXA, and body volume index (BVI). DEXA involves a whole body scanner and two low-dose x-rays. Underwater testing is based on the fact that fat is less dense than lean body mass. The individual is dunked underwater, asked to expel all air from the lungs, and weighed on an underwater scale. Both tests are accurate within 2-3% margin of error. However, the accuracy of underwater testing depends on all air being expelled from the lungs. BVI considers where the weight and the fat are located on the body rather than total weight or total fat content.

In humans, waist-to-hip ratio is also useful as a determination of risk of diabetes, cardiovascular disorders, and hypertension (0.7 is considered normal for women and 0.9 for men).

Diabetes and pre-diabetes are advantageously diagnosed by measuring blood glucose and/or insulin levels. Glucose is generally measured after fast (at least 8 hours post-prandial). A normal fasting plasma glucose level is less than 110 mg per dL (6.1 mmol per L) and normal 2 hr post-prandial glucose (PPG) levels are less than 140 mg per dL (7.75 mmol per L) after 75 g glucose load. Blood glucose levels above the normal level but below the criterion established for diabetes mellitus indicate pre-diabetes or impaired glucose homeostasis. Persons falling into this category have fasting plasma glucose levels ranging from 110 to 126 mg per dL (6.1 to 7.0 mmol per L) and a 2 hr PPG level between 140 mg per dL (7.75 mmol per L) and 200 mg per dL (11.1 mmol per L). Both impaired fasting glucose and impaired glucose tolerance are associated with an increased risk of developing type 2 diabetes mellitus. Diabetes is generally diagnosed at a fasting glucose level higher than 126 mg/dL and a 2 hr PPG of greater than 200 mg/dL. Such criteria are provided, e.g., by the World Health Organization and the American Diabetes Association.

Glucose tolerance tests can also be used to detect the effect of the compounds of the invention on glucose levels. In glucose tolerance tests, the individual's ability to tolerate a standard oral glucose load is evaluated by assessing serum and urine specimens for glucose levels. Blood samples are taken before the glucose is ingested, glucose is given by mouth, and blood or urine glucose levels are tested at set intervals after glucose ingestion.

VII. Administration

In therapeutic uses SOST antagonists generally will be in the form of a pharmaceutical composition containing the antagonist and a pharmaceutically acceptable carrier. Pharmaceutically acceptable carriers are well known in the art and include aqueous solutions such as physiologically buffered saline or other buffers or solvents or vehicles such as glycols, glycerol, oils such as olive oil or injectable organic esters. The selection of a pharmaceutically acceptable carrier will depend, in part, on the chemical nature of the SOST antagonist.

Suitable dosage will depend on the nature of the particular SOST antagonist candidate. By way of example, in dosing it should be noted that systemic injection, either intravenously, subcutaneously or intramuscularly, can be used. Dosing performed by nebulized inhalation, eye drops, or oral ingestion should be at an amount sufficient to produce blood levels of the SOST antagonist candidate similar to those reached using systemic injection. The amount of SOST antagonist candidate that must be delivered by nebulized inhalation, eye drops, or oral ingestion to attain these levels is dependent upon the nature of the inhibitor used and can be determined by routine experimentation.

Administration of a compound of the present invention can be for treatment, in order to reduce weight gain. Administration can also be for maintenance, in order to maintain a subject's weight in a specific range. The dose regimen is dependent on whether the goal is to actively lose weight, or just to maintain weight within a certain range. For example, a dose regimen for actively losing weight will typically involve higher and more frequent doses than for a dose regiment for maintaining weight.

Generally, dosages range from about 0.001 to 1000 mg/kg of body weight of the compound of Formula I. Other doses of the compound of the present invention can be from about 0.01 to about 50 mg/kg of body weight. Still other doses can be from about 0.1 to about 20 mg/kg of body weight. Still some other doses can be from about 0.1 to about 10 mg/kg of body weight. Yet other doses can be about 0.2, 0.3, 0.4, 0.5, 0.6, 0.7, 0.8, 0.9, 1.0, 1.5, 2.0, 2.5, 3.0, 3.5, 4.0, 4.5, 5.0, 5.5, 6.0, 6.5, 7.0, 7.5, 8.0, 8.5, 9.0, 9.5 or 10 mg/kg of body weight. Other doses can be about 15, 20, 25, 30, 35, 40, 45, 50, 55, 60, 65, 70, 75, 80, 85, 90, 95, 100, 200, 300, 400, 500, 600, 700, 800, 900 or 1000 mg/kg of body weight. The compound can be administered at other doses known to one of skill in the art.

The compound of the present invention can be administered as a single administration in a single dose, or over a period of time using several administrations. For example, the compound can be administered in a period of at least one day, or for at least 2, 3, 4, 5, 6 or 7 days. Alternatively, the compound can be administered over a period of at least 1 week, or 2, 3, or 4 weeks. Other administrations can be over a period of at least 1 month, or 2, 3, 4, 5, 6, 7, 8, 9, 10, 11 or 12 months. Still other administrations can be for the life of the subject. In some embodiments, the administration is over a period of at least 7 days. In other embodiments, the administration is over a period of at least 30 days. Other time periods for administration of the compounds are known to one of skill in the art.

When the compound is administered over a period of time, the administration can be of any useful frequency. For example, the administration can be once an hour, or every 2, 3, 4, 5, 6, 7, 8, 9, 10, 11, 12, 13, 14, 15, 16, 17, 18, 19, 20, 21, 22, or 23 hours. Alternatively, the administration can be once a day, or every 2, 3, 4, 5, 6, or 7 days. Other administrations can be once a week, or every 2, 3, or 4 weeks. Still other administrations can be once a month, or less frequent. The compound can be administered at other frequencies known to one of skill in the art.

The dose that is administered to the subject can be for general administration to the entire body, or the dose can be administered to a specific area for targeted administration. Targeted administration can be effected by topical administration or via injection.

Individuals to be treated using methods of the present invention can be any mammal, for example, dog, cat, horse, cow, goat, a commercially important or domesticated animal, or human.

A pharmaceutically acceptable carrier may include physiologically acceptable compounds that act, for example, to stabilize the SOST antagonist or increase its absorption, or other excipients as desired. Physiologically acceptable compounds include, for example, carbohydrates, such as glucose, sucrose or dextrans, antioxidants, such as ascorbic acid or glutathione, chelating agents, low molecular weight proteins or other stabilizers or excipients. One skilled in the art would know that the choice of a pharmaceutically acceptable carrier, including a physiologically acceptable compound, depends, for example, on the route of administration of the SOST antagonist and on its particular physio-chemical characteristics.

Generally, such carriers should be nontoxic to recipients at the dosages and concentrations employed. Ordinarily, the preparation of such compositions entails combining the therapeutic agent with buffers, antioxidants such as ascorbic acid, low molecular weight (less than about 10 residues) polypeptides, proteins, amino acids, carbohydrates including glucose, maltose, sucrose or dextrins, chelating agents such as EDTA, glutathione and other stabilizers and excipients. Neutral buffered saline or saline mixed with nonspecific serum albumin are exemplary appropriate diluents.

The pharmaceutical compositions of the present invention can be prepared for administration by a variety of different routes. In general, the type of carrier is selected based on the mode of administration. Pharmaceutical compositions can be formulated for any appropriate manner of administration, including, for example, topical, oral, nasal, intrathecal, rectal, vaginal, sublingual or parenteral administration, including subcutaneous, intravenous, intramuscular, intrasternal, intracavernous, intrameatal, or intraurethral injection or infusion. A pharmaceutical composition (e.g., for oral administration or delivery by injection) can be in the form of a liquid (e.g., an elixir, syrup, solution, emulsion or suspension). A liquid pharmaceutical composition can include, for example, one or more of the following: sterile diluents such as water for injection, saline solution, preferably physiological saline, Ringer's solution, isotonic sodium chloride, fixed oils that may serve as the solvent or suspending medium, polyethylene glycols, glycerin, propylene glycol or other solvents; antibacterial agents; antioxidants; chelating agents; buffers such as acetates, citrates or phosphates and agents for the adjustment of tonicity such as sodium chloride or dextrose. A parenteral preparation can be enclosed in ampoules, disposable syringes or multiple dose vials made of glass or plastic. The use of physiological saline is preferred, and an injectable pharmaceutical composition is preferably sterile.

In some embodiments, the compound is administered orally. In some embodiments, the compound is administered by injection, e.g., intravenously, subcutaneously, intramuscularly, or intraperitoneally. In some embodiments, the injection is an intraperitoneal injection.

The methods of the present invention include application of SOST antagonists in cocktails including other medicaments, for example, antibiotics, fungicides, and anti-inflammatory agents. Alternatively, the methods may comprise sequential dosing of an afflicted individual with a SOST antagonist and one or more additional medicaments to optimize a treatment regime. In such optimized regimes, the medicaments, including the granulation inhibitor, can be applied in any sequence and in any combination.

The SOST antagonists of the present invention may also be included in slow release formulations for prolonged treatment following a single dose. In one embodiment, the formulation is prepared in the form of microspheres. The microspheres can be prepared as a homogenous matrix of a SOST antagonist with a biodegradable controlled release material, with optional additional medicaments as the treatment requires. The microspheres are preferably prepared in sizes suitable for infiltration and/or injection, and injected systemically, or directly at the site of treatment.

The formulations of the invention are also suitable for administration in all body spaces/cavities, including but not limited to pleura, peritoneum, cranium, mediastinum, pericardium, bursae or bursal, epidural, intrathecal, intraocular, intra-articular, intra-discal, intra-medullary, perispinal, etc.

Some slow release embodiments include polymeric substances that are biodegradable and/or dissolve slowly. Such polymeric substances include polyvinylpyrrolidone, low- and medium-molecular-weight hydroxypropyl cellulose and hydroxypropyl methylcellulose, cross-linked sodium carboxymethylcellulose, carboxymethyl starch, potassium methacrylatedivinylbenzene copolymer, polyvinyl alcohols, starches, starch derivatives, microcrystalline cellulose, ethylcellulose, methylcellulose, and cellulose derivatives, β-cyclodextrin, poly(methyl vinyl ethers/maleic anhydride), glucans, scierozlucans, mannans, xanthans, alzinic acid and derivatives thereof, dextrin derivatives, glyceryl monostearate, semisynthetic glycerides, glyceryl palmitostearate, glyceryl behenate, polyvinylpyrrolidone, gelatine, agnesium stearate, stearic acid, sodium stearate, talc, sodium benzoate, boric acid, and colloidal silica.

Slow release agents of the invention may also include adjuvants such as starch, pregelled starch, calcium phosphate mannitol, lactose, saccharose, glucose, sorbitol, microcrystalline cellulose, gelatin, polyvinylpyrrolidone. methylcellulose, starch solution, ethylcellulose, arabic gum, tragacanth gum, magnesium stearate, stearic acid, colloidal silica, glyceryl monostearate, hydrogenated castor oil, waxes, and mono-, bi-, and trisubstituted glycerides. Slow release agents may also be prepared as generally described in WO94/06416.

The amount of SOST antagonists administered to an individual will depend, in part, on the condition and the extent of the condition. Methods for determining an effective amount of an agent to administer for a diagnostic or a therapeutic procedure are well known in the art and include phase I, phase II and phase III clinical trials, or the Pilot and Pivotal trials (FDA device approval pathway). Generally, an agent antagonist is administered in a dose of about 0.01 to 200 mg/kg body weight when administered systemically. The total amount of SOST antagonist can be administered to a subject as a single dose, either as a bolus or by infusion over a relatively short period of time, or can be administered using a fractionated treatment protocol, in which the multiple doses are administered over a more prolonged period of time. One skilled in the art would know that the concentration of a particular SOST antagonist required to provide an effective amount depends on many factors including the age and general health of the subject as well as the route of administration, the number of treatments to be administered, and the nature of the SOST antagonist. In view of these factors, the skilled artisan would adjust the particular dose so as to obtain an effective amount for efficaciously reducing body weight and/or fat mass in an individual.

The compounds of the present invention can be formulated in a variety of different manners known to one of skill in the art. Pharmaceutically acceptable carriers are determined in part by the particular composition being administered, as well as by the particular method used to administer the composition. Accordingly, there are a wide variety of suitable formulations of pharmaceutical compositions of the present invention (see, e.g., *Remington's Pharmaceutical Sciences*, 20$^{th}$ ed., 2003, supra).

Formulations suitable for oral administration can consist of (a) liquid solutions, such as an effective amount of a compound of the present invention suspended in diluents, such as water, saline or PEG 400; (b) capsules, sachets, depots or tablets, each containing a predetermined amount of the active ingredient, as liquids, solids, granules or gelatin; (c) suspensions in an appropriate liquid; (d) suitable emulsions; and (e) patches. The pharmaceutical forms can include one or more of lactose, sucrose, mannitol, sorbitol, calcium phosphates, corn starch, potato starch, microcrystalline cellulose, gelatin, colloidal silicon dioxide, talc, magnesium stearate, stearic acid, and other excipients, colorants, fillers, binders, diluents, buffering agents, moistening agents, preservatives, flavoring agents, dyes, disintegrating agents, and pharmaceutically compatible carriers. Lozenge forms can comprise the active ingredient in a flavor, e.g., sucrose, as well as pastilles comprising the active ingredient in an inert base, such as gelatin and glycerin or sucrose and acacia emulsions, gels, and the like containing, in addition to the active ingredient, carriers known in the art.

The pharmaceutical preparation can be in unit dosage form. In such form the preparation is subdivided into unit doses containing appropriate quantities of the active component. The unit dosage foam can be a packaged preparation, the package containing discrete quantities of preparation, such as packeted tablets, capsules, and powders in vials or ampoules. Also, the unit dosage form can be a capsule, tablet, cachet, or lozenge itself, or it can be the appropriate number of any of these in packaged form. Pharmaceutical preparations can deliver the compounds of the invention in a sustained release formulation.

For any compound used according to the present invention, a therapeutically effective dose can be estimated initially from cell culture assays or animal models. Toxicity and therapeutic efficacy of such compounds can be determined by standard pharmaceutical procedures in cell cultures or experimental animals, e.g., by determining the $LD_{50}$ (the dose lethal to 50% of the population) and the $ED_{50}$ (the dose therapeutically effective in 50% of the population). The dose ratio between toxic and therapeutic effect is the therapeutic index and can be expressed as the ratio between $LD_{50}$ and $ED_{50}$. Compounds that exhibit high therapeutic indices are generally preferred. The data obtained from these cell culture assays and animal studies can be used in formulating a dosage range that is not toxic for use in human. The dosage of such compounds lies preferably within a range of circulating concentrations that include the $ED_{50}$ with little or no toxicity. The dosage can vary within this range depending upon the dosage form employed and the route of administration utilized. The exact formulation, route of administration and dosage can be chosen by the individual physician in view of the patient's condition (see, e.g., Fingl et al. 1975 In: The Pharmacological Basis of Therapeutics, Ch. 1).

In practicing the methods of the present invention, the pharmaceutical compositions can be used alone, or in combination with other therapeutic or diagnostic agents. The additional drugs used in the combination protocols of the present invention can be administered separately or administered together, such as in an admixture. Where one or more drugs are administered separately, the timing and schedule of administration of each drug can vary. The other therapeutic or diagnostic agents can be administered at the same time as the compounds of the present invention, separately or at different times.

In some embodiments, the additional therapeutic agent is an anti-obesity drug or a therapeutic for reducing percentage body fat. In some embodiments, the additional therapeutic agent is an anti-diabetic agent or a therapeutic directed at insulin dysregulation.

For example, the present compounds can be used with additional agents to increase fat and/or lipid metabolism, providing a method for losing weight, losing fat weight (percentage body fat), lowering body mass index, lowering lipids (such as lowering triglycerides), or treating obesity. Exemplary anti-obesity agents include, without limitation, anorexiants, dopamine agonists, $H_3$-histamine antagonists, 5-HT2c receptor agonists, beta-3 adrenergic receptor agonists, cholecystokinin agonists, anti-epileptic agents, leptin, leptin analogs and leptin receptor agonists, neuropeptide Y (NPY) receptor antagonists and modulators, peptide-YY (PYY) receptor agonists, ciliary neurotrophic factor, thyroid hormone receptor-beta agonists, cannabinoid CB1 receptor antagonists, melanin-concentrating hormone receptor antagonists, pancreatic and gastric lipase inhibitors, and combinations thereof. Additional examples include Phentermine, Sibutramine (Meridia), and Orlistat (Xenical). Examples of lipid lowering agents include bile acid sequestrants, fibric acid derivatives, nicotinic acid, and HMGCoA reductase inhibitors. Specific examples include statins such as LIPITOR™, ZOCOR™, PRAVACHOL™, LESCOL™, MEVACOR™, and pitavastatin (nisvastatin) (Nissan, Kowa Kogyo, Sankyo, Novartis) and extended release forms thereof, such as ADX-159 (extended release lovastatin), as well as Colestid, Locholest, Questran, Atromid, Lopid, and Tricor.

Anti-diabetic agents include insulin, thiazolidinedione and non-thiazolidinedione insulin sensitizers, which decrease peripheral insulin resistance by enhancing the effects of insulin at target organs and tissues. Additional anti-diabetic agents include sulfonylureas (e.g., glyburide), biguanides (e.g. metformin), DPP-4 inhibitors (e.g., sitagliptin), incretin analogs (e.g., exenatide), meglitinides (e.g., Nateglinide), and α-glucosidase inhibitors (e.g., acarbose).

Moreover, the present invention can be used in combination with additional anti-obesity therapies. These include anti-obesity agents, as described above, as well as non-pharmaceutical approaches. Examples include reduced caloric intake, increased physical activity, as well as surgeries aimed at reducing body weight, such as liposuction and gastric bypass.

VIII. EXAMPLES

Example 1

Reduction of Body Weight with Ellipticine

In order to determine the effect of ellipticine and ellipticine derivatives in reducing body weight, ellipticine hydrochloride was administered to mice every weekday for 4 weeks (30 days) and their body weights tracked. Ellipticine hydrochloride was solubilized in saline and administered via intraperitoneal injection. Animals were weighed weekly.

The mice had an initial body weight of 30 g prior to treatment. Mice (6 per group) were divided into seven groups and given one of the following treatments:
1. 10 mg ellipticine hydrochloride/kg body weight (Low)
2. 20 mg ellipticine hydrochloride/kg body weight (Mid)
3. 30 mg ellipticine hydrochloride/kg body weight (High)
4. Saline
5. 3 mg/kg body weight (Positive control 2)
6. 5 mg/kg body weight (Positive control low)
7. 10 mg/kg body weight (Positive control high)

The results of the test are illustrated in FIG. 1, which shows the average weight loss for each treatment. Even at the low dose, the animals lost more than 18% of their body weight by the end of the 4 weeks. The middle dose resulted in a weight loss of more than 33% at the end of week 3, resulting in the animal being sacrificed. The highest dose resulted in a 28% reduction in body weight at the end of week 2, resulting in the animal being sacrificed.

Although the foregoing invention has been described in some detail by way of illustration and example for purposes of clarity of understanding, one of skill in the art will appreciate that certain changes and modifications can be practiced within the scope of the appended claims. In addition, each reference provided herein is incorporated by reference in its entirety to the same extent as if each reference was individually incorporated by reference.

What is claimed is:

1. A method for reducing the body weight of a subject in need thereof, comprising administering to the subject a therapeutically effective amount of a compound having the formula:

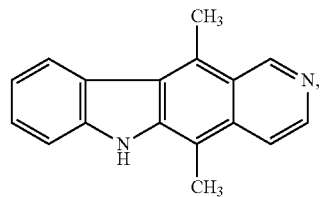

and
salts, hydrates and isomers thereof, thereby reducing the body weight of an individual.

2. The method of claim 1, wherein the compound is the salt.

3. The method of claim 1, wherein the compound is the hydrochloride salt.

4. The method of claim 1, wherein the administration is by injection.

5. The method of claim 4, wherein the administration is by intraperitoneal injection.

6. The method of claim 1, wherein the administration is oral.

7. The method of claim 1, wherein the administration is for at least seven days.

8. The method of claim 7, wherein the administration is for at least 30 days.

9. The method of claim 1, wherein the compound is administered at a dose of from about 0.1 mg/kg to about 100 mg/kg.

10. The method of claim 9, wherein the compound is administered to the subject at a dose of from about 0.1 mg/kg to about 50 mg/kg.

11. The method of claim 1, wherein the administration results in a reduction of percentage body fat in the individual.

12. The method of claim 1, wherein the individual is diabetic.

13. The method of claim 1, wherein the compound is administered in combination with an additional anti-obesity therapy.

14. The method of claim 1, wherein the compound is administered in combination with an anti-diabetes agent.

15. The method of claim 1, wherein the administration is topical.

16. The method of claim 1, wherein the administration is via a patch.

* * * * *